(12) United States Patent
Håland et al.

(10) Patent No.: US 10,746,715 B2
(45) Date of Patent: Aug. 18, 2020

(54) AIR POLLUTION MONITORING

(71) Applicant: InnoSense AS, Kjeller (NO)

(72) Inventors: Stian Håland, Kjeller (NO); Morgan Kjølerbakken, Kjeller (NO); Franck René Dauge, Kjeller (NO); Terje Grøntoft, Kjeller (NO); Torbjørn Heltne, Kjeller (NO)

(73) Assignee: InnoSense AS, Kjeller (NO)

( * ) Notice: Subject to any disclaimer, the term of this patent is extended or adjusted under 35 U.S.C. 154(b) by 96 days.

(21) Appl. No.: 15/780,471

(22) PCT Filed: Nov. 30, 2016

(86) PCT No.: PCT/GB2016/053762
§ 371 (c)(1),
(2) Date: May 31, 2018

(87) PCT Pub. No.: WO2017/093728
PCT Pub. Date: Jun. 8, 2017

(65) Prior Publication Data
US 2018/0356381 A1    Dec. 13, 2018

(30) Foreign Application Priority Data

Dec. 1, 2015 (GB) .................................. 1521199.8

(51) Int. Cl.
*G01N 33/00* (2006.01)
*G01N 27/416* (2006.01)
*G01N 27/417* (2006.01)

(52) U.S. Cl.
CPC ....... *G01N 33/006* (2013.01); *G01N 27/4162* (2013.01); *G01N 27/4175* (2013.01); *G01N 33/0016* (2013.01)

(58) Field of Classification Search
CPC .............. G01N 33/006; G01N 33/0016; G01N 27/4175; G01N 27/4162
See application file for complete search history.

(56) References Cited

U.S. PATENT DOCUMENTS 5,418,131 A * 5/1995 Butts ...................... C12M 41/14
  236/2
6,022,138 A * 2/2000 Sonander ............... G01N 25/68
  374/28

(Continued)

FOREIGN PATENT DOCUMENTS

JP  2009128221 A  6/2009
KR 20160129773 A  11/2016

OTHER PUBLICATIONS

International Search Report; European Patent Office; International Application No. PCT/GB2016/053762; dated Apr. 10, 2017; 6 pages.

(Continued)

Primary Examiner — Akm Zakaria
(74) Attorney, Agent, or Firm — Taft Stettinius & Hollister LLP (57) ABSTRACT

An air monitoring system for analysing an air sample including: a duct arranged such that the air sample flows therethrough from an inlet to an outlet; a relative humidity sensor arranged to measure a relative humidity of the air sample; a heating module including a first heater arranged to heat the air sample; a temperature sensor arranged to measure a temperature of the air sample; a controller arranged selectively to operate the first heater if the measured relative humidity is above an upper threshold; and an analysis module including at least one chemical analysis transducer providing an output corresponding to a presence or concentration of a predetermined substance in the air sample.

19 Claims, 11 Drawing Sheets

(56) References Cited

U.S. PATENT DOCUMENTS

| | | | |
|---|---|---|---|
| 2006/0191319 A1* | 8/2006 | Kurup | G01N 33/24 73/23.34 |
| 2011/0077545 A1* | 3/2011 | Eichler | A61B 5/097 600/538 |
| 2011/0177403 A1 | 7/2011 | Usami et al. | |
| 2013/0152608 A1* | 6/2013 | Wray | F16L 55/1003 62/50.7 |
| 2014/0260692 A1* | 9/2014 | Sharp | G01N 1/2273 73/863.23 |

OTHER PUBLICATIONS

Written Opinion of the International Searching Authority; European Patent Office; International Application No. PCT/GB2016/053762; dated Apr. 10, 2017; 7 pages.

* cited by examiner

AIR POLLUTION MONITORING

CROSS REFERENCE TO RELATED APPLICATIONS

This application is a U.S. national stage filing of International Application No. PCT/GB2016/053762 filed Nov. 30, 2016, which claims priority to U.K. Application No. 1521199.8 filed Dec. 1, 2015, the contents of each application incorporated herein by reference in their entirety.

TECHNICAL FIELD

The present invention relates to air monitoring systems, more specifically small scale air monitoring systems that can be implemented at a relatively small cost compared to conventional air monitoring systems known in the art per se.

BACKGROUND

Over the course of the last two centuries the developed world has become increasingly industrialised. While this has brought unprecedented rates of technological advancement, it has also been responsible for some drastic changes in our environment, particularly the quality of air. These pollutants often arise from the burning of fossil fuels in power stations and vehicles, manufacturing products, and other industrial processes. Furthermore, pollutants can also enter the atmosphere from natural sources including from volcanic eruptions, dust storms, forest and grassland fires, living vegetation, and sea spray.

While the causes of climate change are often contested, it is widely agreed that pollutants such as ozone, nitrogen dioxide, sulphur dioxide, and particulates—often broken down into coarse particulate matter less than 10 microns in diameter (commonly denoted as $PM_{10}$) and fine particulate matter less than 2.5 microns in diameter (commonly denoted as $PM_{2.5}$)—are not desirable for a number of reasons. Air pollution has been linked with disease, death to humans, damage to other animals and plant life including food crops, and damage to both the natural and built environments.

Environmental monitoring, particularly air quality monitoring, has therefore assumed increased importance in recent years. Air monitoring systems are highly important for monitoring the level of various pollutants within the air, particularly around industrialised areas or areas that typically have a lot of vehicular traffic that may be outputting undesirable substances into the surrounding air.

Conventional air monitoring systems contain a large amount of equipment for monitoring the air quality of the surroundings. For example, they typically house a number of different instruments for measuring air quality such as sample probes, filters, gas conditioning systems, a number of gas analysers that are used to check for the presence of different pollutants such as $NO_2$ and $SO_2$, and particulate matter samplers used to monitor for $PM_{10}$ and $PM_{2.5}$ particulates. These systems are typically installed on industrial sites and proximate to roads in order to monitor the quality of the air in areas that are of concern.

Conventional air monitoring systems are usually large, self-contained units that resemble storage containers. The size of these systems makes them difficult to transport and install. These conventional systems are also typically very expensive, rendering it uneconomic to install large quantities of them in order to cover a wider area.

There are microsensor systems on the market that can provide an indication of air quality that are a fraction of the size of the above-mentioned systems. However, the Applicant has appreciated that these microsensor systems are typically not sufficiently accurate and reliable for use in environmental monitoring, where accurate and reliable measurements are of paramount importance. In particular the Applicant has appreciated that existing smaller scale microsensor based systems are typically very sensitive to changes in their operating temperature as well as the temperature and relative humidity of the air samples taken.

SUMMARY

When viewed from a first aspect the present invention provides an air monitoring system for analysing an air sample, the air monitoring system comprising:
  a duct arranged such that the air sample flows therethrough from an inlet to an outlet;
  a relative humidity sensor arranged to measure a relative humidity of the air sample;
  a heating module including a first heater arranged to heat the air sample;
  a temperature sensor arranged to measure a temperature of the air sample;
  a controller arranged selectively to operate the first heater if the measured relative humidity is above an upper threshold; and
  an analysis module including at least one chemical analysis transducer providing an output corresponding to a presence or concentration of a predetermined substance in the air sample.

Thus it will be appreciated by those skilled in the art that the present invention provides an improved, more robust air monitoring system in which air passes through an internal duct and past one or more chemical analysis transducers which are arranged to provide an indication of the presence or concentration of substances e.g. pollutants present within the air. If the relative humidity of the air sample is determined to be too high, the air is heated prior to entering the analysis module to bring the relative humidity down, thus making the air sample safe to flow through the analysis module. For example, the Applicant has appreciated that if the transducers used in typical microsensors are exposed to excessive quantities of moisture—typically 80% or more relative humidity, depending on the sensor—they are usually destroyed. There may also be an optimal range of relative humidity that is advantageous for the system to operate within, perhaps for reasons of efficiency.

It has also been found that by keeping the air sample within a specific relative humidity and, at least in some embodiments, temperature range(s), the measurements taken are accurate enough to be used for environmental modelling without being unduly influenced by errors due to being outside ideal operating range(s). This allows smaller scale sensors to be used even in applications where accuracy is important.

Those skilled in the art will appreciate that there are a number of transducers that can be used to determine the presence of particular substances within an air sample known in the art per se. In a set of embodiments, the chemical analysis transducer comprises an electrochemical cell. An electrochemical cell typically comprises: an electrolyte; a working electrode; a counter electrode; and a reference electrode. In the presence of a particular analyte such as $NO_x$ or $SO_2$ for which the electrolyte is specifically chosen, the amount of current that flows from the working electrode to the counter electrode via the electrolyte will vary which is then detected.

In an alternative set of embodiments, the chemical analysis transducer comprises a chemo-resistive device. In a subset of such embodiments, the chemo-resistive device comprises a metal-oxide-semiconductor (MOS) device. These chemo-resistive based devices comprise a semiconducting material such as one or more metal oxides or metal sulphides as a sensing layer disposed between a pair of electrodes. The semiconducting material is specifically chosen to detect a particular gas, for example $SnO_2$, $ZnO$, $WO_3$ and $Fe_2O_3$ which can be used to detect oxidizing or reducing gases. The chemo-resistive device is heated locally and once the substance to be detected comes into contact with the surface, a chemical reaction takes place which involves an interaction between the oxygen adsorbed within the sensing layer at its surface and the gas within the air sample alters the population of electrons and holes i.e. charge carriers within the chemo-resistive device. This change in charge carrier density will then alter the conductivity of the device and this can be detected as is known in the art per se.

As well as preventing the over-hydration of the transducers or ensuring humidity is not too high for efficient operation, the Applicant has also appreciated the importance of maintaining the temperature of the air sample above a lower threshold or "freeze point". In a set of embodiments, the controller is further arranged selectively to operate the first heater if the measured temperature is below a lower threshold. This, too, could ensure that the transducer remains in an optimum window, but in some embodiments the lower threshold could be a freeze prevention threshold. This advantageously prevents the transducer becoming too cold through exposure to the air sample regardless of the measured relative humidity of the air sample.

It will be appreciated by those skilled in the art that there are many different controller types known per se from control theory that could readily be employed in accordance with the present invention. However, in a particular set of embodiments the controller comprises a proportional-integral-derivative (PID) controller. The Applicant has appreciated that PID controllers are particularly well suited to the control of heaters in such an air monitoring system due to their relatively low response times, as well as being relatively inexpensive and simple to implement and providing a high degree of configurability.

Optionally, the duct, humidity sensor, temperature sensor and the heater are situated within a housing, which may provide protection to sensitive electronics as well as allowing simple transport and relocation.

In an alternative set of embodiments, the controller is further arranged dynamically to operate the first heater using a machine learning algorithm. This algorithm is used to analyse the temperature and/or relative humidity data in order to determine how to operate the first heater. This advantageously allows the controller to use e.g. pattern recognition techniques to "learn" from past temperature and/or relative humidity data and make predictions about future events, such as typical fluctuations in temperature of relative humidity throughout a given time cycle, e.g. a day, a year etc. In some further embodiments, the machine learning algorithm takes inputs from one or more sensors external to the housing. These external sensors can provide data regarding e.g. rain and wind, which can be used to further "train" the machine learning algorithm, e.g. improving the ability to stabilise temperature, or minimizing fluctuations from the electrochemical cells.

Optionally, the machine learning algorithm is implemented at least partially in a remote server to which an air monitoring system is in data communication. In such embodiments, data is sent from the air monitoring system to the remote server, which processes it using the machine learning algorithm in order to operate the controller. This may, for example, allow for greater processing power to be provided by an external processor than the processing power available locally to the controller. This also allows data to be shared via the remote server to other monitoring stations in other locations. Where external sensors are used, the data therefrom may also be sent to the remote server for input to the machine learning algorithm. As well as the external sensors that may form part of the system, in some embodiments, the remote server takes inputs from independent external data sources. This advantageously allows the machine learning algorithm to utilise data from e.g. weather forecasting or nowcasting services.

In a set of embodiments, the system is arranged to compensate for the measured relative humidity. Additionally or alternatively, in some embodiments, the system is arranged to compensate for the measured temperature. Thus as well as operating the controller based on the measured relative humidity and optionally the measured temperature, these values may be used in the calculation of the output regarding the presence or concentration of the predetermined substance in the air sample.

In a set of embodiments, the analysis module comprises a second heater and a second temperature sensor arranged to measure a temperature of at least part of the analysis module itself, wherein the second heater is operable to vary the temperature of the analysis module. This advantageously prevents the situation wherein the air sample has a dew point higher than the temperature of the analysis module. If this happens, moisture from the air sample may condense when it comes into contact with the analysis module, which may cause damage to the analysis module. In some such embodiments, the analysis module further comprises an analysis module control loop arranged selectively to operate the second heater based if the measured temperature of the analysis module is lower than a condensation prevention threshold.

This condensation prevention threshold may be absolute, however in some embodiments the condensation prevention threshold is set dynamically based on a dew point of the air sample determined by the relative humidity sensor. In some such embodiments, the condensation prevention threshold is set to a value greater than the measured temperature of the analysis module by a predetermined buffer value. This allows the system to determine how close the temperature of the analysis module is permitted to be to the dew point of the air sample.

Those skilled in the art will appreciate that there are a number of heaters which could readily be employed in accordance with the present invention. In some embodiments at least one, preferably both where applicable, of the first and second heaters comprises a heating element and an associated heat transfer member. In such embodiments, the heat transfer member serves to transfer heat energy from the heating element to the air sample and/or analysis module as appropriate. In a subset of such embodiments, the heating element comprises a resistive heating element. The first and second heating elements could be distinct from one another but equally they could be the same—i.e. provided by a single physical component, operated in either the same or in different heating modes (e.g. operated at different power levels). Similarly the first and second heat transfer members could be distinct or the same.

In a set of embodiments, the heat transfer member comprises a thermally conductive, chemically inert material. It is advantageous for the heat transfer member to provide good thermal conductivity for transferring heat energy from the heating element to the air sample and/or analysis module while being chemically inert so as not to react with the pollutants and/or any moisture content within the air sample. Additionally or alternatively, in some embodiments the heat transfer member comprises a plurality of folds and/or fins. In some embodiments, the heat transfer member comprises an inert coating. Additionally or alternatively, in some embodiments, the heat transfer member comprises an inert plating. This inert coating could, by way of example only, comprise polytetrafluoroethylene (PTFE), fluorinated ethylene propylene (FEP), perfluoroalkoxy alkanes (PFA) or some other inert polymer. An inert plating may, by way of example only, comprise gold.

In another, overlapping set of embodiments at least one of the first and second heaters comprises a Peltier element. Peltier elements can advantageously be used to both heat and cool their surroundings depending on the direction in which current is passed therethrough. Accordingly in a set of embodiments the system is arranged to apply cooling to the air sample in the event that it exceeds an upper temperature threshold. Of course other methods of cooling than use of a Peltier device could be employed.

In some embodiments, the controller is arranged selectively to ensure the air sample is not cooled below the dew point of the air sample.

In some embodiments, the air monitoring system further comprises thermally insulating material between the heating module and the analysis module. This may help to prevent heat from the first heater within the heating module from influencing the temperature of the analysis module which may be temperature-sensitive. In some further embodiments, the air monitoring system further comprises thermally insulating material between the analysis and heating modules and an external housing. This is to isolate the analysis module from the temperature of the external housing and thus ambient conditions (hot or cold) in order to prevent external temperature variations affecting the measurements carried out within the system.

In contrast to the thermally insulating material outlined above, in some embodiments the analysis module comprises thermally conductive material between the chemical analysis transducer and the duct. This thermally conductive material may be used to enhance thermal coupling between the air sample and the transducer(s), reduce the influence of temperature on measurements taken and limit the temperature gradient across the transducer(s) and any other electronics within the system. Having low gradients improves the precision of temperature measurements. If the temperature of the temperature sensor, the chemical analysis transducer and the associated electronics are similar, compensating for the influence of temperature is also made simpler. Another benefit of enclosing the chemical analysis transducers in such a material is that it reduces air convection induced fluctuations in the temperature of the chemical analysis transducer(s), thus lowering the noise associated with such fluctuations.

Additionally or alternatively, at least in some embodiments the analysis module comprises electrically conductive material between the at least one chemical analysis transducer and the duct. Preferably, the electrically conductive material completely surrounds the at least one chemical analysis transducer and electronics and is connected to a known potential e.g. to ground. This is particularly advantageous as it reduces the chance of electromagnetic interference disturbing the chemical transducers and any associated electronic circuitry.

The controller may be used to control the operation of the first and/or second heaters in order to vary the temperature of the air sample and/or analysis module respectively. There are a number of possible ways of controlling the heater(s) to obtain a desired temperature. In some embodiments, the controller is arranged to alternate the respective heater on and off with a variable duty cycle to adjust the temperature of the air sample.

The Applicant has appreciated that there are different microsensor-based relative humidity sensors available on the market. In one set of embodiments, the relative humidity sensor comprises a micro-electromechanical systems (MEMS) based sensor. MEMS based sensors are particular advantageous because of their small size, relatively low cost and high accuracy. In an alternative set of embodiments, the relative humidity sensor comprises a thin-film based sensor.

BRIEF DESCRIPTION OF THE FIGURES

Certain embodiments of the invention will now be described, by way of example only, with reference to the accompanying drawings in which.

DETAILED DESCRIPTION OF THE ILLUSTRATIVE EMBODIMENTS

Figure 1:
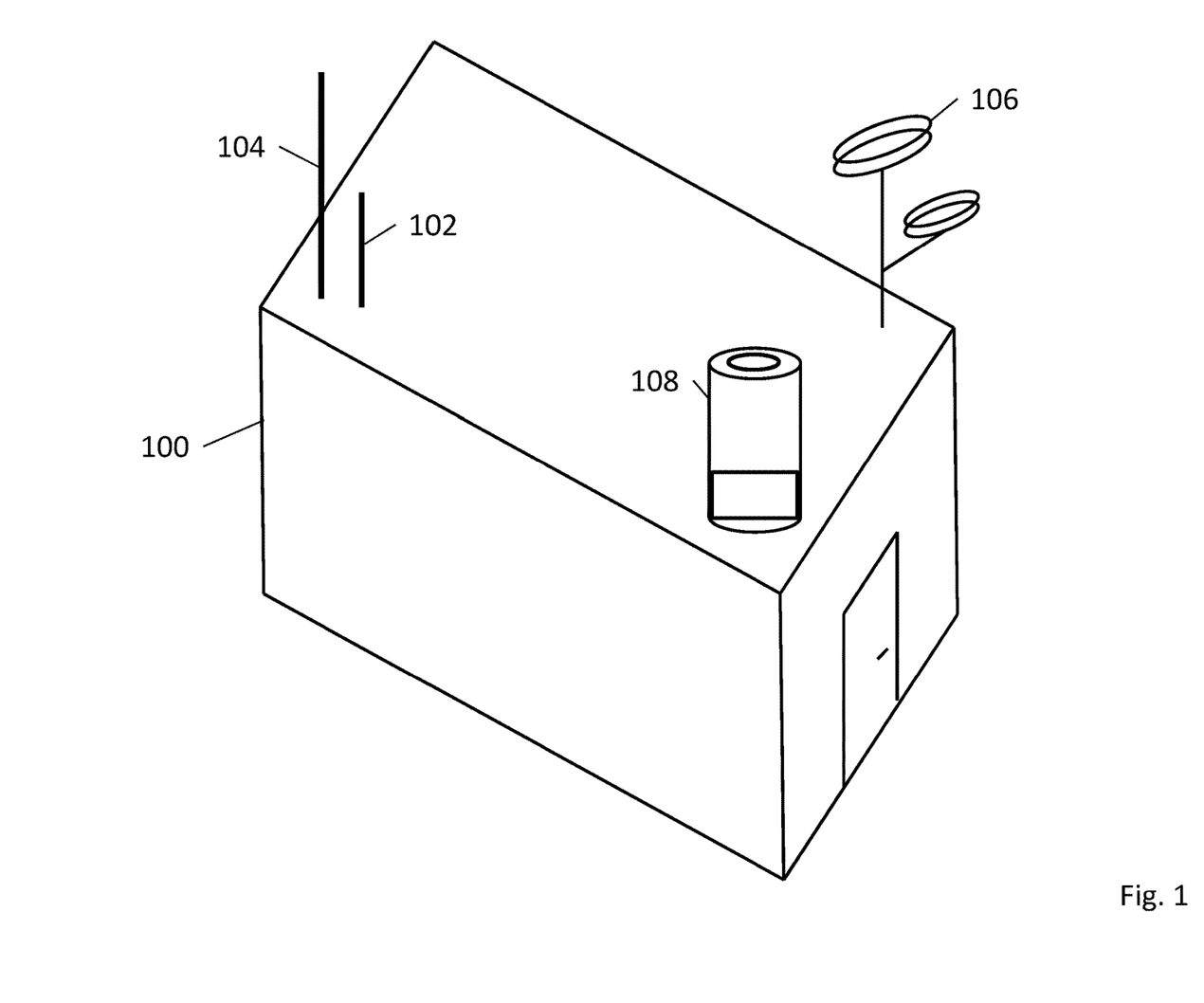
FIG. 1 shows a diagrammatic representation of a conventional air monitoring system.

FIG. 1 shows a conventional air monitoring system 100. This air monitoring system 100 is implemented in a large storage container like structure. The system 100 has a number of independent instruments 102, 104, 106, 108 located therein, each used for determining the presence of a different pollutant within an air sample.

Figure 2:
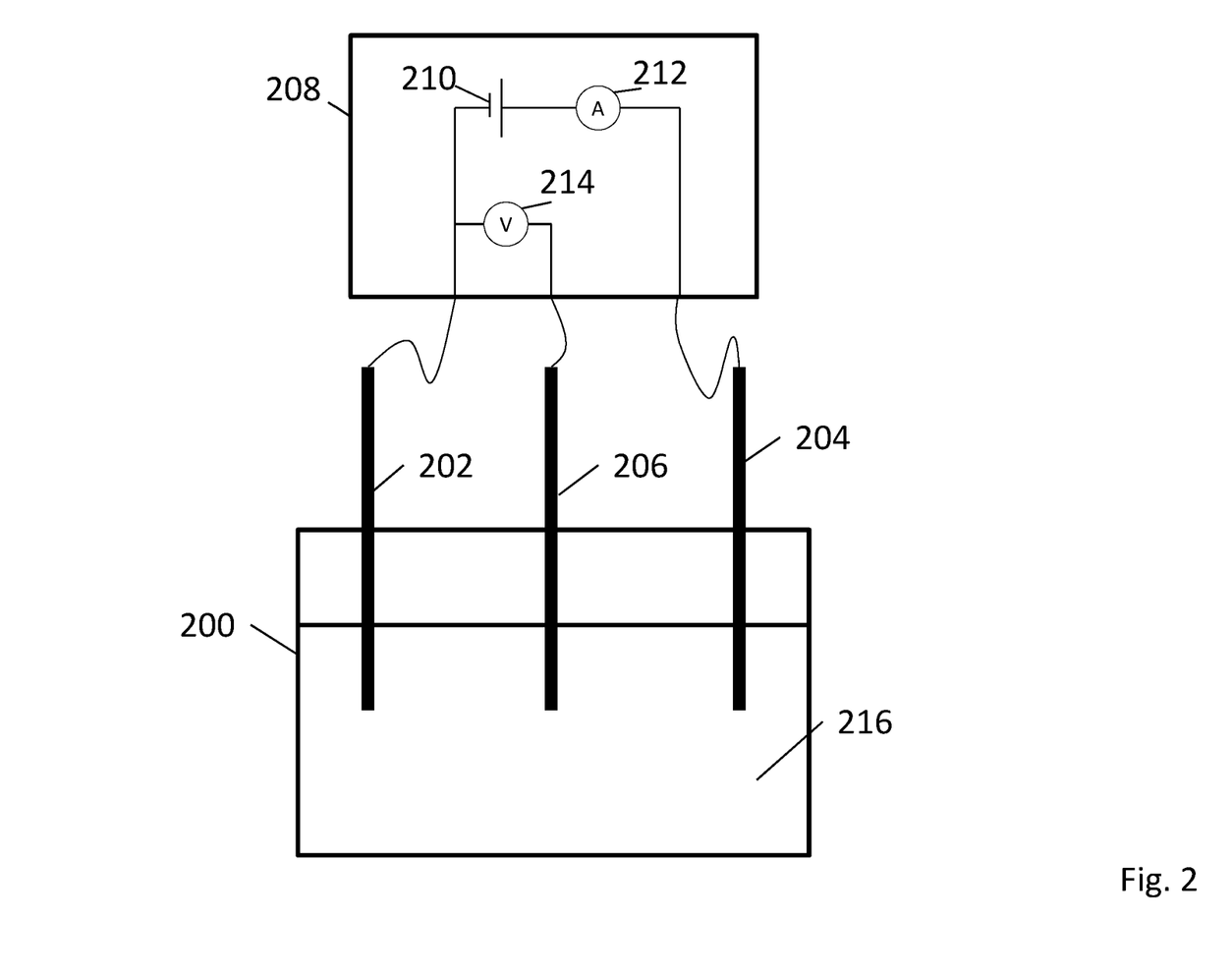
FIG. 2 shows a typical electrochemical cell.

FIG. 2 shows a typical electrochemical cell 200 as can be used with embodiments of the present invention. The electrochemical cell 200 contains an electrolyte 216 which is specifically chosen for the detection of a given pollutant and is usually a mineral acid.

The electrochemical cell 200 also contains three electrodes: a working electrode 202; a counter electrode 204 (sometimes referred to as an auxiliary electrode); and a reference electrode 206. A potential difference is applied using a voltage source 210 across the working 202 and counter 204 electrodes, and the resulting current that flows is measured by an ammeter 212. In the presence of the pollutant to be detected, the rates of oxidation and reduction at these two electrodes 202, 204 change and thus the current also changes.

As current flows through the electrochemical cell 200, it is difficult to maintain a constant potential at the counter electrode due to the ongoing redox reactions taking place. In order to account for this, the potential difference between the reference electrode 206, which has a known reduction potential, and the working electrode 202 is measured using a voltmeter 214. However, this operation may be carried out using e.g. a potentiostat circuit as is known in the art per se.

However, such an electrochemical cell 200 is particularly sensitive to temperature and relative humidity as will be described further below with reference to FIG. 3.

Figure 3:
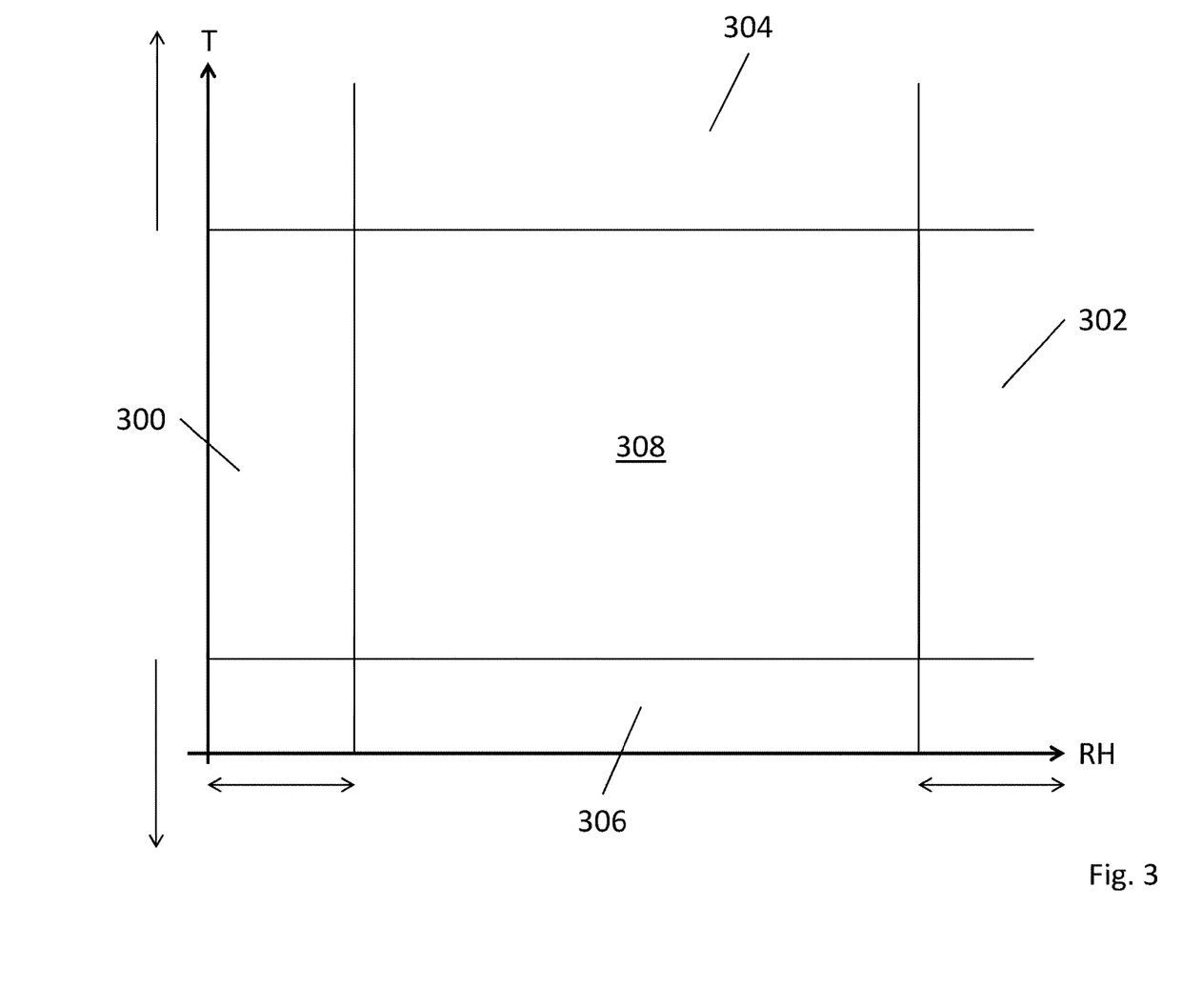
FIG. 3 is a graph which illustrates the operating envelope of a typical electrochemical cell.

FIG. 3 illustrates the operating envelope of the electrochemical cell 200 shown in FIG. 2 as a graph wherein the y-axis represents temperature T, while the x-axis represents relative humidity RH. There are a number of shaded regions 300, 302, 304, 306 in which the electrochemical cell will either cease to operate correctly or even become damaged. The operating envelope 308 is defined inside these extreme ranges, and it is this window 308 in which the electrochemical cell 200 should be operated within this envelope at all times.

The first shaded region 306 corresponds to the temperature T being too low. In this situation the electrochemical cell 200 is too cold and the electrolyte 216 may even freeze. This prevents the cell from functioning correctly as chemical reactions occur more slowly with lower temperatures. Also, in the case of the electrolyte 216 being frozen, the reactions may not occur at all. In this situation, the temperature 7' must be raised in order to continue operation. However, it would still be preferable to prevent the situation from happening by ensuring that air samples that pass the electrochemical cell 200 are not too cold.

The second shaded region 304 corresponds to the temperature T being too high. If the electrochemical cell 200 is exposed to high temperatures, it may begin to burn and become permanently damaged. This is highly undesirable and thus air samples that are passed through the electrochemical cell 200 should not be too high in temperature. This could be achieved by applying cooling to the air samples that are too hot, or temporarily closing an inlet to the cell.

The third shaded region 300 corresponds to the relative humidity RH being too low. In this situation, the electrochemical cell 200 becomes dehydrated and will cease to function. This situation, while undesirable, can be rectified by rehydrating the cell 200.

The fourth shaded region 302 corresponds to the relative humidity RH being too high. In this situation, the electrochemical cell 200 becomes over-saturated with water and can become permanently damaged. This situation is extremely undesirable as it can render the air monitoring station unable to detect the corresponding pollutant. It is thus highly important to ensure that air passing the electrochemical cell 200 does not have too high a relative humidity RH value. Typically, a relative humidity RH of over 80% will permanently damage the electrochemical cell 200. As will be explained below, this is achieved by heating the incoming air sample to reduce its relative humidity.

By way of example only, the lower and upper temperature thresholds may be −30° C. and 50° C. respectively. The lower and upper relative humidity thresholds may be 15% RH and 90% RH respectively. However, it will be appreciated that these values are subject to the properties of the specific electrochemical cell 200 (or other type of chemical analysis transducer) chosen.

Figure 4:
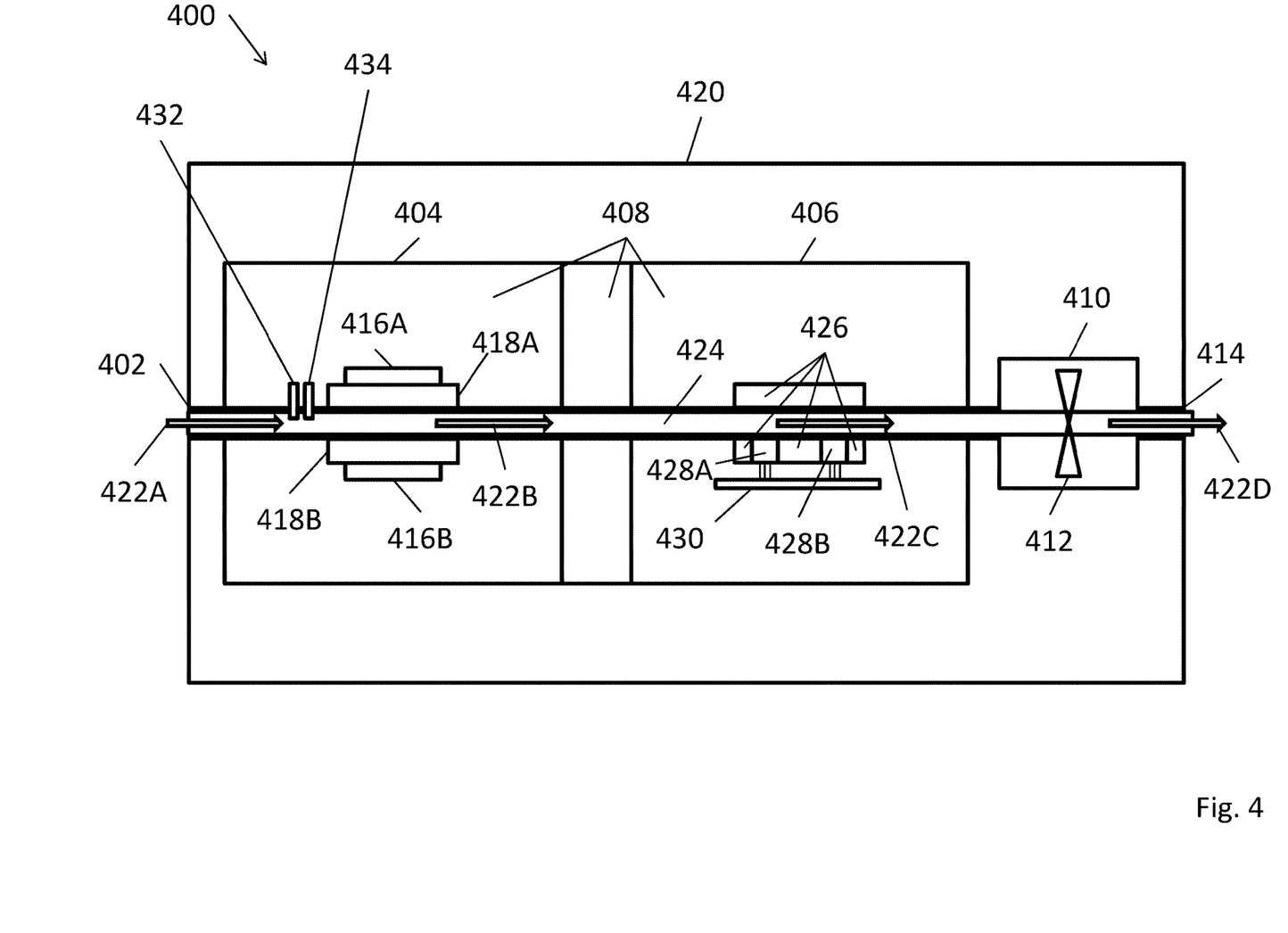
FIG. 4 shows a block diagram of an air monitoring system in accordance with an embodiment of the present invention.

FIG. 4 shows a block diagram of an air monitoring system 400 in accordance with an embodiment of the present invention. This air monitoring system 400 is designed in order to try and maintain operation within the operating envelope 308 as described above, avoiding the extreme temperatures and relative humidities.

At the centre of the system 400 is a duct 424 that runs from an inlet 402 to an outlet 414, allowing air samples to pass through the system. As air samples pass through the system, they traverse a heating module 404 and an analysis module 406, each of which will be described in further detail below. Air samples are drawn through the duct from the inlet 402 to the outlet 414 by a mechanical fan 412 that is situated within a fan module 410. The entire system 400 is situated within a housing enclosure 420 which protects the internal components from exposure to the outside environment.

The heating module 404 contains a pair of resistive heaters 416A, 416B which are situated either side of the duct 424. Between the resistive heaters 416A, 416B and the duct 424 are a pair of heat exchangers 418A, 418B. A controller (not shown) acts to selectively operate the resistive heaters 416A, 416B based on data obtained from a temperature sensor 432 and a relative humidity sensor 434 disposed downstream of the heaters 416A, 416B that provides feedback regarding the temperature and relative humidity of the air sample 422B after heating.

The analysis module 406 contains a pair of electrochemical cells 428A, 428B similar to the electrochemical cell 200 described above with reference to FIG. 2 and are each arranged to detect a different pollutant. These electrochemical cells 428A, 428B are connected to analysis electronics 430. These analysis electronics 430 include an analogue front-end for connection to the electrochemical cells 428A, 482B and an analogue-to-digital converter (ADC). The analysis electronics 430 are arranged to convert the current from the electrochemical cells 428A, 428B and the measurements (e.g. voltages) from the temperature and relative humidity sensors 432, 434 to digital values. These digital values may be processed locally or may be processed by a remote server as described with reference to FIG. 8.

The electrochemical cells 428A, 428B are surrounded by a thermally and electrically conductive material 426. This material 426 increases the thermal coupling between the air sample 422B and the electrochemical cells 428A, 428B. The material 426 also serves to limit the temperature gradient across the cells 428A, 428B and the analysis electronics 430.

The heating module 404 and the analysis module 406 are surrounded by thermally insulating material 408. This insulating material 408 sits between and around each of the modules 404, 406 and reduces the ability for heat energy from one module to affect the other. This insulating material 408 also helps to isolate the external housing 420 from the external environment, thus preventing external temperature fluctuations affecting measurements taken by the system.

In use, an incoming air sample 422A enters the system through the inlet 402 and is drawn through the heating module 404 by the fan 412. If the controller determines that the relative humidity of the air sample 422A is too high, it switches on the resistive heaters 416A, 416B. The heat exchangers 418A, 418B conduct heat energy from the heaters 416A, 416B to the air efficiently. This heating raises the temperature of the air sample, such that a heated air sample 422B can then safely be drawn into the analysis module 406 by the fan 412.

After heating, the air sample 422O enters the analysis module 406, wherein it is passed through the electrochemical cells 428A, 428B for analysis. The analysis electronics 430 observe the operating current for each cell 428A, 428B such that the system 400 can record data pertaining to the presence and/or concentration of each pollutant and can raise an alert if an excessive quantity of any such pollutant is detected.

After analysis, the fan 412 then draws the air sample through the fan housing 410 before exhausting it through the outlet 414 and back to the atmosphere 422D.

Figure 5:
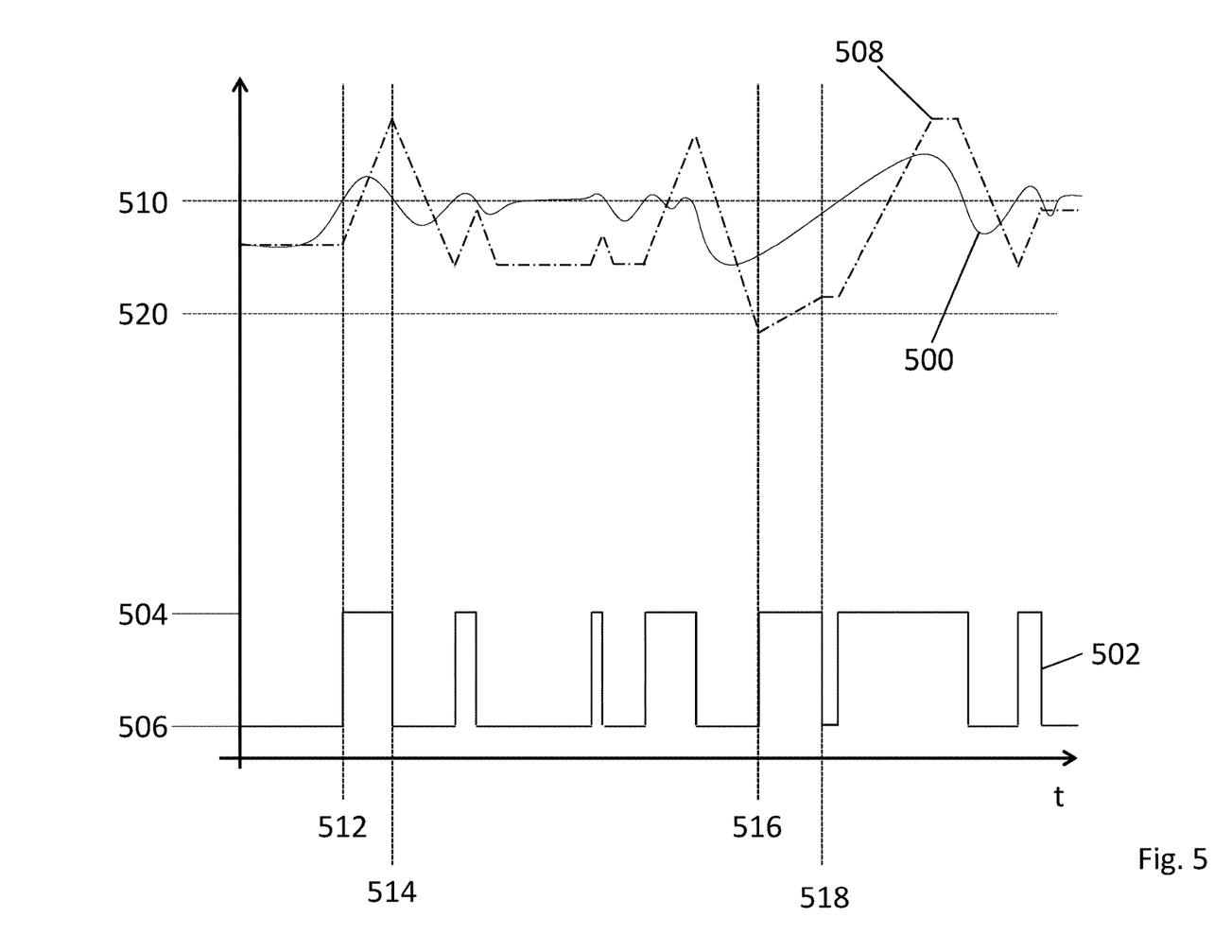
FIG. 5 shows a graph of the operation of the heater and the relative humidity of air samples as they pass through the air monitoring system of FIG. 4.

FIG. 5 shows a graph of the operation of the heaters 416A, 416B and the relative humidity of air samples as they pass through the heating module 404 within the air monitoring system of FIG. 4. The graph shows the operation of the heaters 416A, 416B over a period of time t.

Shown in the graph is a plot 500 of the relative humidity RH over a period of time. As can be seen from the graph, it fluctuates above and below a threshold humidity value 510. When the relative humidity RH exceeds this threshold 510, the controller decides that the heaters 416A, 416B must be switched on to prevent damage to the electrochemical cells 428A, 428B.

The operation of the heaters 416A, 416B is shown on the graph as plot 502. As can be seen from the graph, in this particular embodiment the controller operates the heaters 416A, 416B using on-off or "bang-bang" control, switching them between the "on" state 504 and the "off" state 506.

This on-off control of the heaters 416A, 416B controls the temperature of the air samples as they pass through the heating module 404. The temperature over time is shown in the graph as plot 508.

As an example, at time 512, using data from the relative humidity sensor 434 the controller determines that the relative humidity 500 of the air sample 422A entering the system has exceeded the threshold 510. The controller switches the heaters 416A, 416B to the on state 504 accordingly. The temperature 508 of the air sample 422A then steadily increases, which causes a reduction in the relative humidity 500 of the air sample 422A.

At a subsequent time 514, the relative humidity value 500 has dropped below the threshold 510 and the controller switches the heaters 416A, 416B back to the off state 506, causing the temperature 508 to decline.

At a later time 516, the controller determines using data from the temperature sensor 432 that the air sample 422A is too cold, having fallen below the freeze prevention threshold 520. The controller again decides to switch the heaters 416A, 416B to the on state 504 in order to prevent the electrochemical cells 428A, 428B from becoming excessively cold. Once the air sample 422A is sufficiently warm at time 518, the heaters 416A, 416B are once again switched to the off state 506.

As illustrated in the graph, this operation then continues and the controller switches the heaters 416A, 416B on and off as required with the fluctuating relative humidity and temperature of the air as it comes into the system 400.

Figure 6:
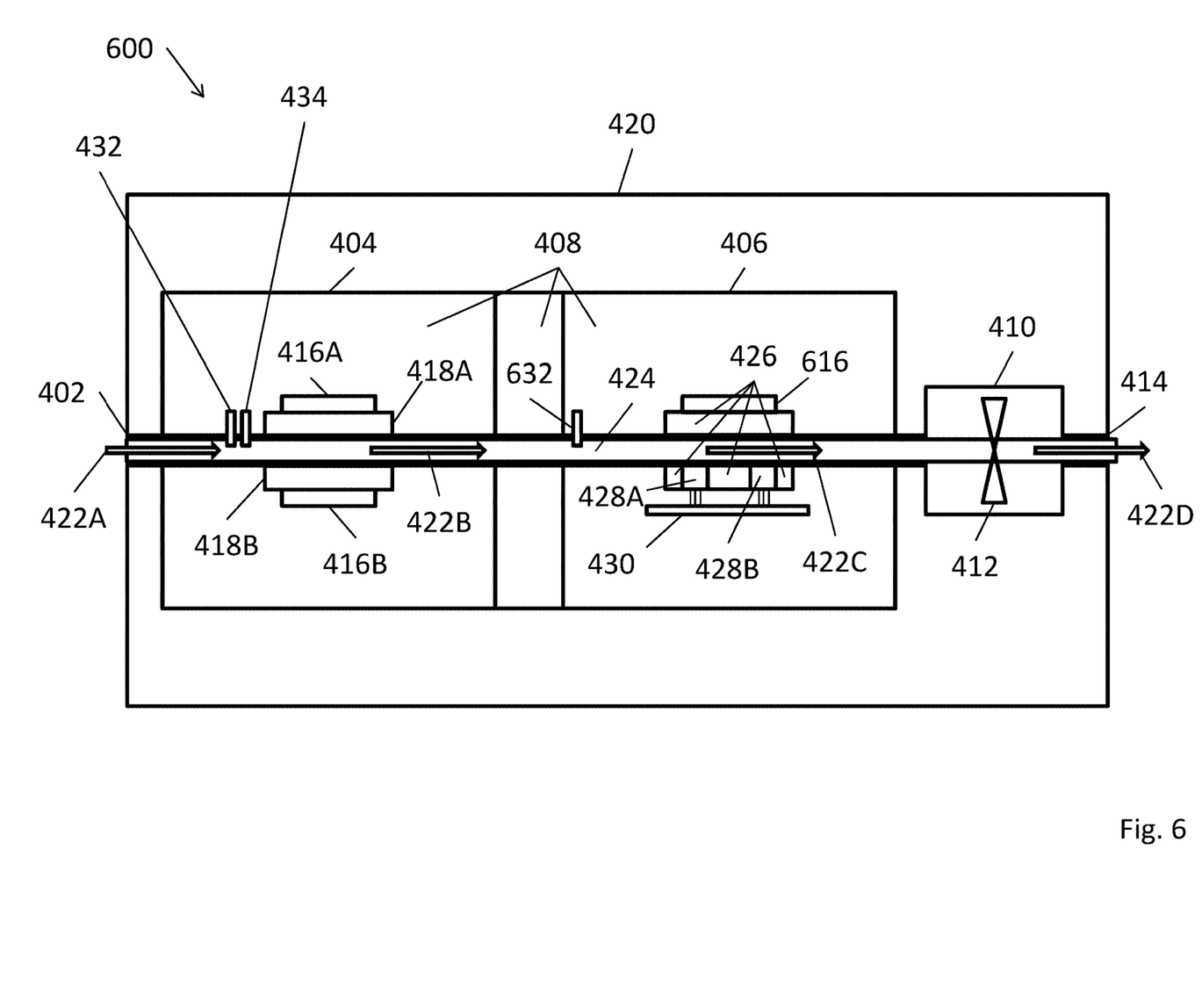
FIG. 6 shows a block diagram of a further embodiment of the present invention.

FIG. 6 shows a block diagram of a further embodiment of the present invention, wherein the use of the same reference numerals indicate like components to those already described hereinabove with reference to FIG. 4. However, in this embodiment, the analysis module 406 includes an additional heater in the form of a Peltier element 616 and a further temperature sensor 632.

The Peltier element 616 is arranged such that current can be run through it in either direction to run it as a heater or a cooler as appropriate. If, for example, the controller determines from the temperature sensor 632 in the analysis module 406 that the temperature of the analysis module 406 is less than the dew point of the heated air sample 422B that is to enter said analysis module 406, the controller can operate the Peltier element 616 as a heater in order to prevent condensation forming on the electrochemical cells 428A, 428B which may cause damage. Similarly if the temperature of the module 406 is too high, the Peltier element 616 can be operated in reverse mode to cool it.

Figure 7:
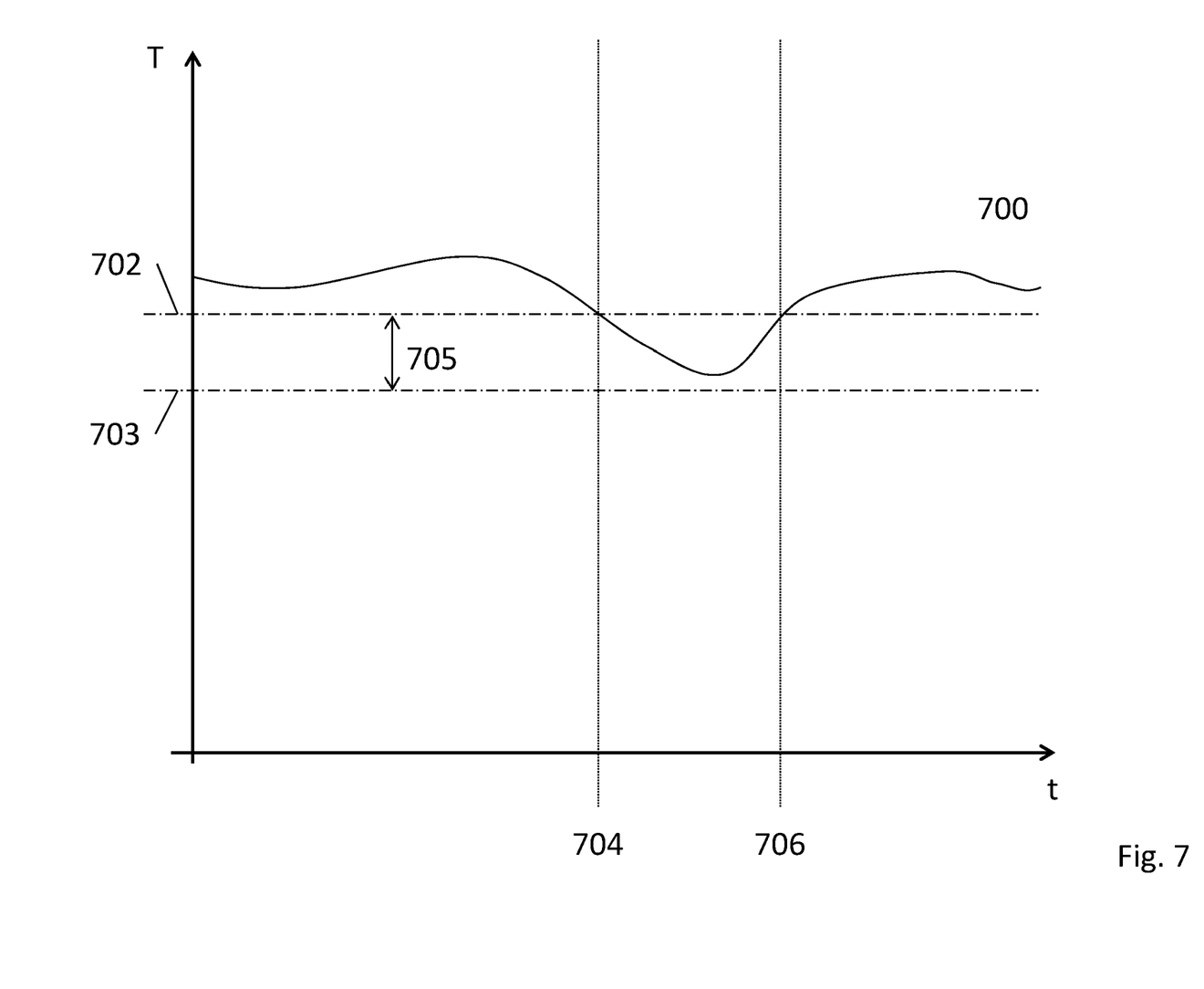
FIG. 7 shows a graph of the operation of the Peltier element within the air monitoring system of FIG. 6.

FIG. 7 shows a graph of the operation of the Peltier element 616. Shown on the graph is a plot 700 of the temperature T of the analysis module 406 as a function of time t. Also shown on the graph is the dew point 703 of the air sample 422B which is to enter the analysis module 406. For the sake of clarity, the dew point 703 is shown to be constant in FIG. 7; however it will be appreciated that in reality this may vary with time due to fluctuations in relative humidity. The system has a built in condensation prevention threshold temperature 702, which is greater than the dew point by a buffer 705. This buffer means that the Peltier element 616 can be used to heat the analysis module early enough that the analysis module 406 will not actually reach the dew point 703.

Initially the temperature T of the analysis module 406 is above the condensation prevention threshold 702. However at time 704, the temperature of the analysis module 406 drops below the threshold 702. At this time, the controller switches the Peltier element 616 on, which acts to heat the analysis module 406. This begins to raise the temperature T of the analysis module 406.

At a subsequent time 706 the temperature T of the analysis module 406 is above the threshold 702 once more and so the controller turns the Peltier element 616 off again.

Figure 8:
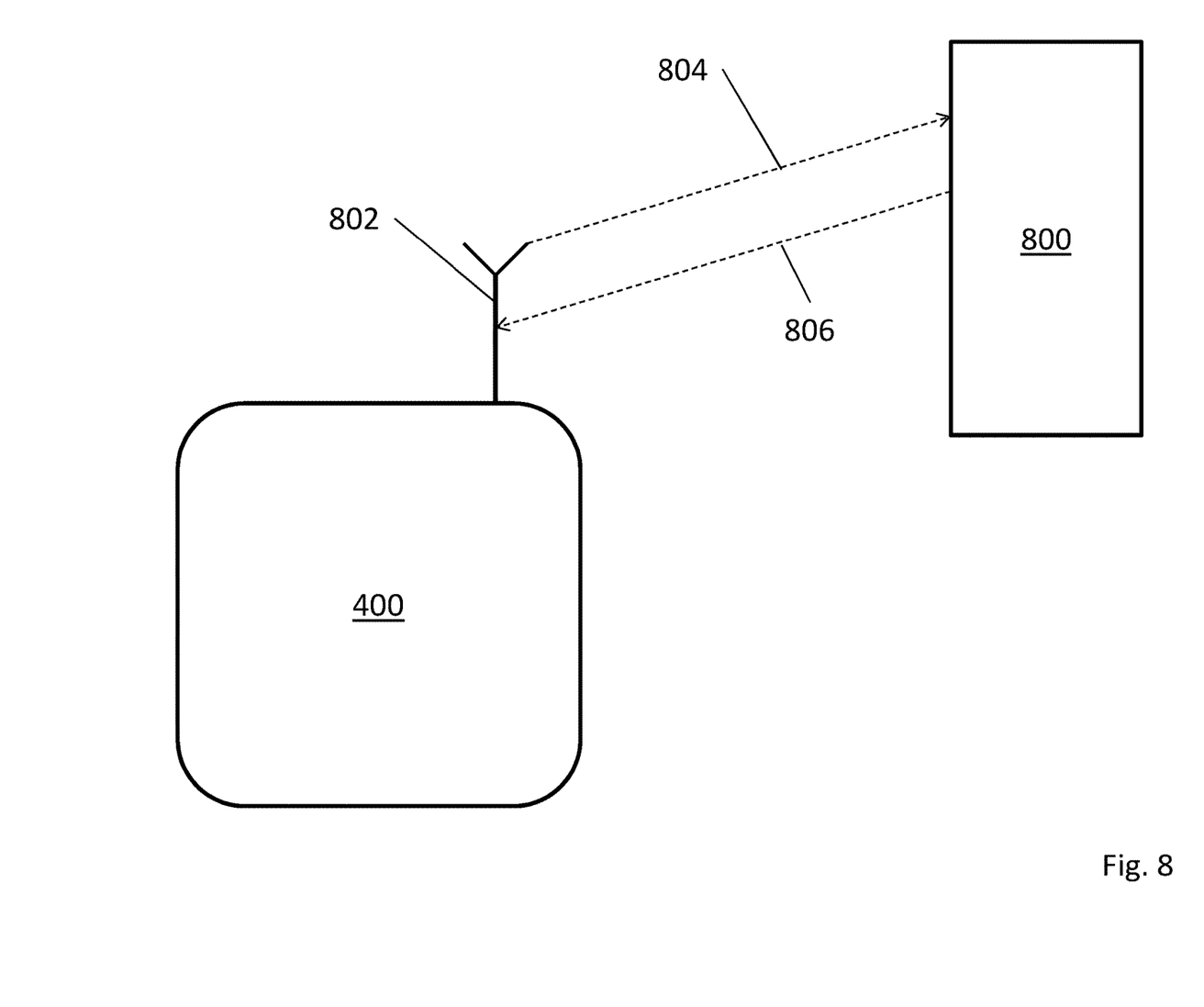
FIG. 8 shows a connection between an air monitoring system of the present invention and a remote server.

FIG. 8 shows a connection between an air monitoring system 400 in accordance with the present invention and a remote server 800. The air monitoring system 400 in this particular embodiment is provided with an antenna 802 for wireless communications, though it is envisaged that wired communications could also be readily used. This antenna 802 provides means for communicating with the remote server 800.

The air monitoring system 400 transmits temperature and/or relative humidity data 804 to the remote server 800. The remote server then carries out data processing using e.g. a machine learning algorithm, and then decides on the temperature thresholds to be applied by the controller in order to keep the system 200 within the operating envelope 308.

Figure 9:
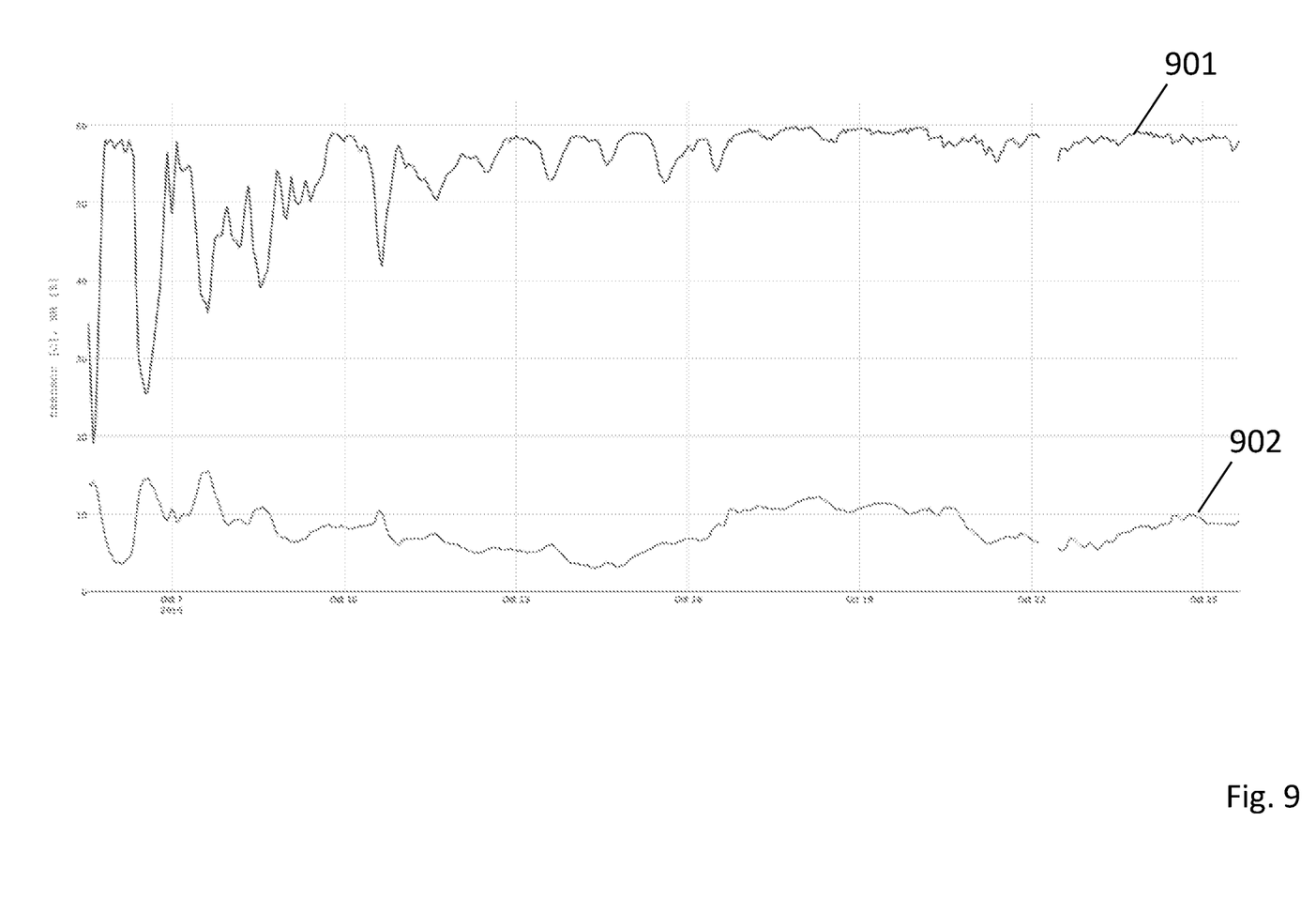
FIG. 9 is a graph of sensor module temperature and relative humidity of the air flowing through the sensor module of an air monitoring system in accordance with an embodiment of the present invention.

FIG. 9 shows a graph of data collected from a prototype of an air monitoring system embodying the present invention constructed by the Applicant. The relative humidity of the air flowing through the sensor module 901 and the sensor module temperature 902 can be seen to converge to stable values, within the operating limits of the system, over time.

Figure 10:
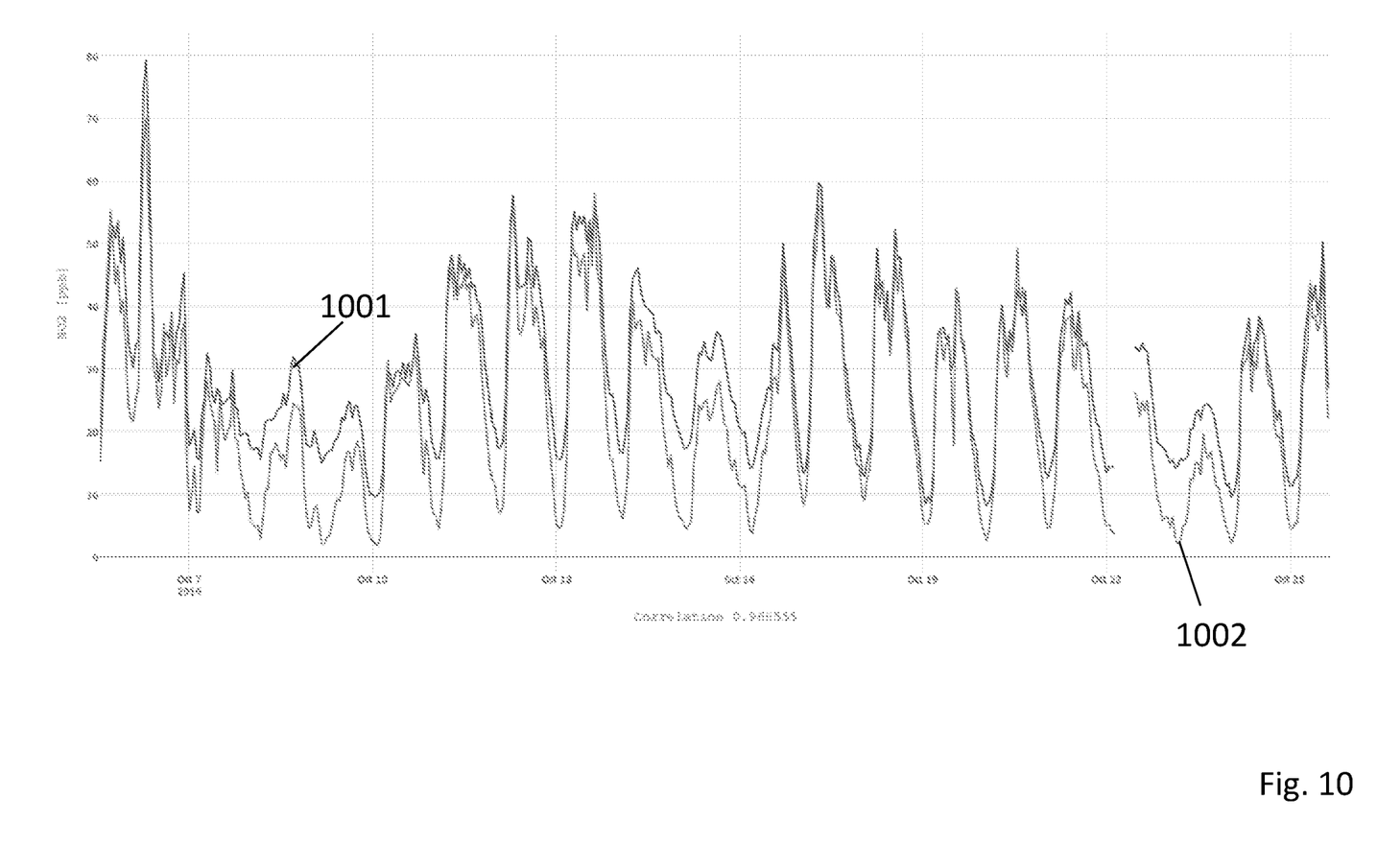
FIG. 10 is a graph of $NO_2$ concentration over time as measured by the sensor module of an air monitoring system in accordance with an embodiment of the present invention as compared to $NO_2$ concentration measured by a reference instrument.

FIG. 10 shows a graph of $NO_2$ concentration 1001 over time as measured by the sensor module of the prototype as compared to $NO_2$ concentration 1002 as measured by a reference instrument of high precision. It will be noted that there is a high degree of correlation between the two.

Figure 11:
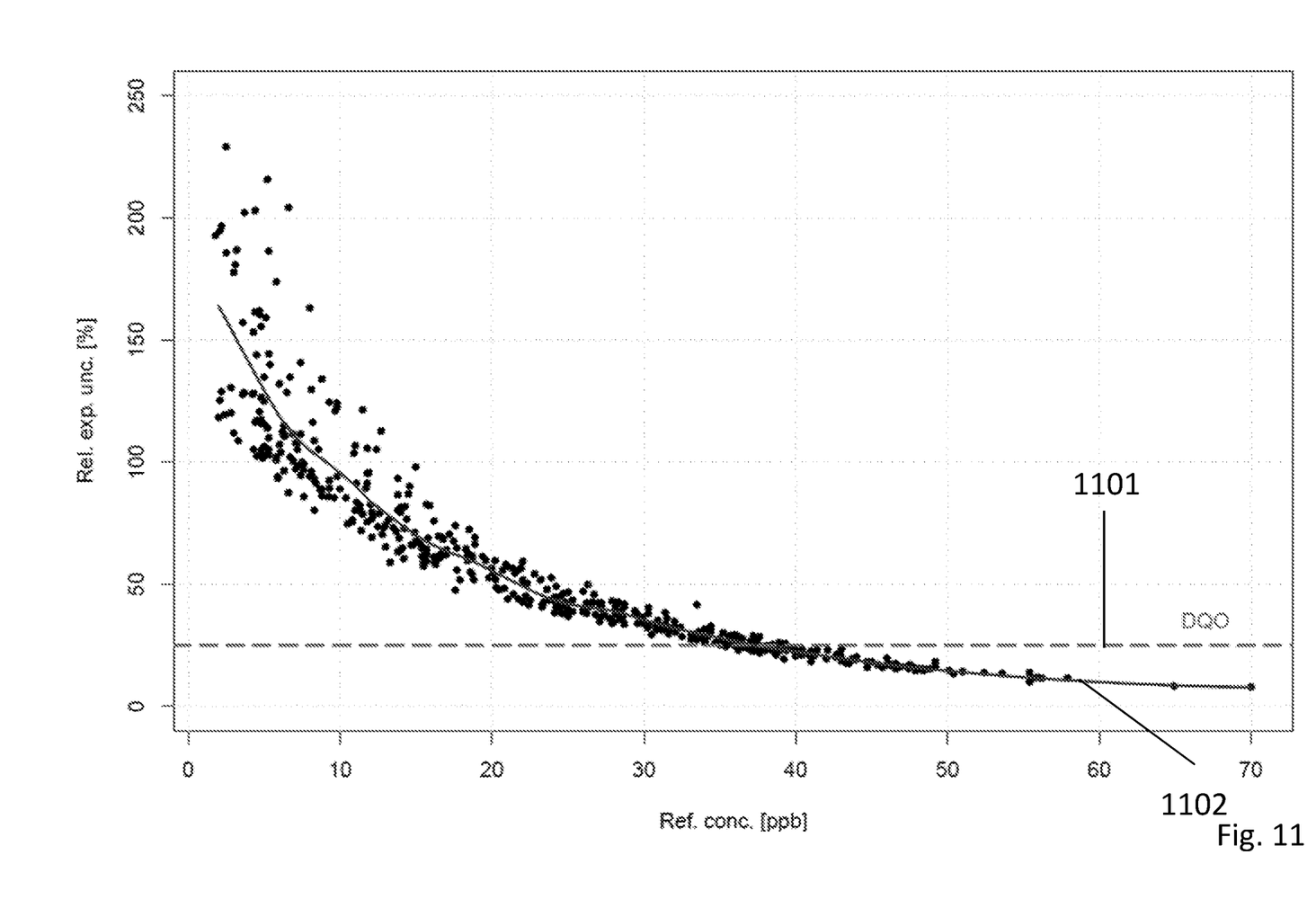
FIG. 11 shows the relative expanded uncertainty of an air monitoring system in accordance with an embodiment of the present invention.

FIG. 11 shows the relative expanded uncertainty 1101 vs measured level of an air monitoring system in accordance with an embodiment of the present invention. The DQO (Data Quality Objective) 1101 is an EU limit for indicative measurements and the uncertainty should be below this limit (25%) at the limit value of measured pollutant, which for $NO_2$ is 200 µg/m³ corresponding to about 105 ppb The system according to the invention exceeds this requirement, meeting the DQO at around 40 ppb.

Thus it will be seen that an improved air monitoring system for detecting pollutants within an air sample that is more reliable and less susceptible to damage due to variations in temperature and/or relative humidity of said air sample has been described herein. Although particular embodiments have been described in detail, it will be appreciated by those skilled in the art that many variations and modifications are possible using the principles of the invention set out herein.

The invention claimed is:

1. An air monitoring system for analysing an air sample, the air monitoring system comprising:
   a duct arranged such that the air sample flows therethrough from an inlet to an outlet;
   a relative humidity sensor arranged to measure a relative humidity of the air sample;
   a heating module including a first heater arranged to heat the air sample;
   a temperature sensor arranged to measure a temperature of the air sample;
   a proportional-integral-derivative controller arranged selectively to operate the first heater if the measured relative humidity is above an upper threshold; and
   an analysis module including at least one chemical analysis transducer providing an output corresponding to a presence or concentration of a predetermined substance in the air sample;
   wherein at least the duct, the relative humidity sensor, the heating module and the temperature sensor are enclosed in a housing and the controller is arranged dynamically to operate the first heater using a machine learning algorithm taking inputs from one or more sensors external to the housing.

2. The air monitoring system as claimed in claim 1, wherein the chemical analysis transducer comprises an electrochemical cell.

3. The air monitoring system as claimed in claim 1, wherein the chemical analysis transducer comprises a chemo-resistive device.

4. The air monitoring system as claimed in claim 1, wherein the controller is further arranged selectively to operate the first heater if the measured temperature is below a lower threshold.

5. The air monitoring system as claimed in claim 1 comprising thermally insulating material between the analysis and heating modules and said housing.

6. The air monitoring system as claimed in claim 1, wherein the machine learning algorithm is implemented at least partially in a remote server to which said temperature and relative humidity sensors are in data communication, the remote server receiving additional input from one or more independent data sources.

7. The air monitoring system as claimed in claim 1, arranged to compensate for the measured relative humidity.

8. The air monitoring system as claimed in claim 1, arranged to compensate for the measured temperature.

9. The air monitoring system as claimed in claim 1, wherein the first heater comprises a first heating element and a first heat transfer member.

10. The air monitoring system as claimed in claim 9, wherein the first heat transfer member comprises a thermally conductive, chemically inert material.

11. The air monitoring system as claimed in claim 9, wherein the first heat transfer member comprises a plurality of folds and/or fins.

12. The air monitoring system as claimed in claim 1, wherein the first heater comprises a Peltier element.

13. The air monitoring system as claimed in claim 1, arranged to apply cooling to the air sample in the event that it exceeds an upper temperature threshold.

14. The air monitoring system as claimed in claim 1, wherein the controller is arranged selectively to ensure the air sample is not cooled below the dew point of the air sample.

15. The air monitoring system as claimed in claim 1, comprising thermally insulating material between the heating module and the analysis module.

16. The air monitoring system as claimed in claim 1, further comprising thermally conductive material between the chemical analysis transducer and the duct.

17. The air monitoring system as claimed in claim 1, wherein the analysis module comprises electrically conductive material between the at least one chemical analysis transducer and the duct, the electrically conductive material completely surrounding the at least one chemical analysis transducer and electronics associated with the at least one chemical analysis transducer and being connected to a known potential.

18. The air monitoring system as claimed in claim 1, wherein the relative humidity sensor comprises a micro-electromechanical systems (MEMS) based sensor.

19. The air monitoring system as claimed in claim 1, wherein the relative humidity sensor comprises a thin-film based sensor.

* * * * *